United States Patent [19]

Miederer et al.

[11] Patent Number: 4,871,481
[45] Date of Patent: Oct. 3, 1989

[54] PREPARATION OF 1,4-DIAMINO-2,3-DICYANOANTHRAQUINONE

[75] Inventors: Peter Miederer, Hassloch; Eberhard Michaelis, Weingarten, both of Fed. Rep. of Germany

[73] Assignee: BASF Aktiengesellschaft, Ludwigshafen, Fed. Rep. of Germany

[21] Appl. No.: 137,826

[22] Filed: Dec. 24, 1987

[30] Foreign Application Priority Data

Dec. 31, 1986 [DE] Fed. Rep. of Germany ....... 3644824

[51] Int. Cl.⁴ ............................................. C07C 97/24
[52] U.S. Cl. .................................................... 552/239
[58] Field of Search ............................................ 260/378

[56] References Cited

U.S. PATENT DOCUMENTS

| 901,059 | 7/1862 | Braun et al. | 260/378 |
| 1,938,029 | 12/1933 | Kugel | 260/378 |
| 4,294,769 | 10/1981 | Kröck et al. | 260/378 |
| 4,299,771 | 11/1981 | Takeshita et al. | 260/378 |
| 4,661,292 | 4/1987 | Schaulin et al. | 260/378 |

FOREIGN PATENT DOCUMENTS

| 1475602 | 4/1967 | France | 260/378 |
| 2183668 | 6/1987 | United Kingdom | 260/378 |

Primary Examiner—Glennon H. Hollrah
Assistant Examiner—Raymond Covington
Attorney, Agent, or Firm—Oblon, Spivak, McClelland, Maier & Neustadt

[57] ABSTRACT

1,4-Diaminoanthraquinone-2-sulfonic acid or salts thereof are reacted with cyanide ions at pH 8–11 in the presence of oxidizing agents in a mixture of water and 1-methoxy-2-propanol, 2-methoxy-1-propanol, N,N-dimethylformamide, N,N-dimethylacetamide, N,N-dimethylpropionamide, dimethyl sulfoxide, dioxane, N-methylpyrrolidone or mixtures thereof, the ratio water: organic liquid being $\geq 3:1$, the reaction proceeding at higher concentrations than in a purely aqueous medium and producing appreciably purer products in a high space-time yield.

18 Claims, No Drawings

PREPARATION OF 1,4-DIAMINO-2,3-DICYANOANTHRAQUINONE 1,4-Diamino-2,3-dicyanoanthraquinone, hereinafter also referred to as diaminodinitrile, is an important starting material for preparing blue anthraquinonoid dyes. There are various known ways of preparing the dinitrile.

For instance, DE-A-No. 3,039,262 mentions the reaction of 1,4-diaminoanthraquinone-2-sulfonic acid, referred to hereinafter as diaminoacid, or a salt thereof, of 1,4-diamino-2-cyananthraquinone, or of 1,4-diaminoanthraquinone-2,3-disulfonic acid, or a salt thereof, in an aqueous medium with a cyanide ion donor in the presence of quaternary ammonium compounds.

According to Examples 1 and 3, the amounts used, based on diaminoacid, are 3.3 times the weight in the case of benzyltriethylammonium chloride and 5.5 times the weight in the case of lauryltrimethylammonium chloride. Working up reaction mixtures containing such amounts of unwanted organic ballast presents problems. Disposal in the effluent constitutes substantial pollution with organic carbon and is not acceptable on economic grounds either. Nor is an additional treatment of the effluent by extraction with an organic solvent, as indicated, a commercially viable alternative.

DE-A-No. 2,931,981 describes the reaction of 1,4-diaminoanthraquinone-2-sulfonic acid or 1,4-diaminoanthraquinone-2,3-disulfonic acid with cyanide ion donors in formamide to give diaminodinitrile. Leaving aside the fact that the stated yields are not reproducible, this process is likely to give rise to high solvent and effluent costs or, if the cyanide-containing solvent is to be regenerated, substantial technical complexity, associated with corresponding costs.

Aqueous processes for preparing diaminodinitrile from diaminoacid by reaction with salts of hydrocyanic acid in the presence or absence of oxidizing agents are described in DE-C-Nos. 536,998 and 1,108,704. On account of a high dilution, the diaminoacid:water ratio being 1:50, the space-time yields obtainable by this process are very low. The process also has the disadvantage that the product contains more than 10% by weight of interfering by-products such as 1,4-diaminoanthraquinone, 1.4-diamino-2-cyanoanthraquinone (monoitrile) and 1,4-diaminoanthraquinone -2,3-dicarboximide, depressing the yield of desired product. According to Examples 1 to 4 of DE-C-No. 1,108,704, high excesses of sodium cyanide compared with the diaminoacid are necessary (diaminoacid:sodium cyanide=1:7.5 to 1:9.5 mole). This causes increased expenses for material and for destroying the excess cyanide.

SUMMARY OF THE INVENTION

It is an object of the present invention to provide a process for preparing diaminodinitrile from diaminoacid which requires no costly effluent treatment and which, while giving a good space-time yield, gives a better grade of product than the prior art processes.

We have found that this object is achieved when the reaction with sodium cyanide to give the dinitrile is carried out in a specific aqueous reaction medium.

The present invention accordingly provides a process for preparing 1,4-diamino-2,3-dicyanoanthraquinone by reacting 1,4-diaminoanthraquinone-2-sulfonic acid or a salt thereof with cyanide ions in water within the pH range 8–11 in the presence of an oxidizing agent at elevated temperature, which comprises carrying out the reaction in mixture of water an 1-methoxy-2-propanol, 2-methoxy-1-propanol, N,N-diamethylformamide, N,N-dimethylacetamide, N,N-dimethylpropionamide, dimethyl sulfoxide, dioxane, N-methylpyrrolidone or a mixture thereof, the ratio of water:organic liquid being $\geq 3:1$ parts by weight.

DETAILED DESCRIPTION OF THE PREFERRED EMBODIMENTS

This favorable effect of the reaction medium according to the invention on the reaction was not foreseeable. Even if, instead of the organic liquids mentioned, for example other alcohols are used, such as ethylene glycol, ethylene glycol monomethyl ether, diethylene glycol monomethyl ether, ethylene glycol monobutyl ether, diethylene glycol monobutyl ether, ethylene glycol monophenyl ether, n-propanol, isobutanol, n-butanol, n-pentanol, dispropylene glycol monomethyl ether or disproylene glycol monoisopropyl ether, the reaction generally takes longer and the yields are appreciably lower than, for example, if a 1-methoxy-2-propanol/water mixture is used.

The organic liquid and water mixture according to the invention makes it possible to carry out the cyanation reaction at higher concentrations than in a purely aqueous medium. As a result, the selectivity of the reaction increases and the end product, diaminodinitrile, is obtained in higher purity and at the same time in a high space-time yield. Furthermore, the addition of the organic liquids according to the invention has a positive effect on the reaction time. By contrast to the reaction in a purely aqueous medium or in mixtures of water and other solvents, the reaction proceeds significantly more rapidly in the process according to the invention, which additionally has a favorable effect on the space-time yield.

In general, the process according to the invention is carried out as follows: the diaminoacid is added to the reaction medium, which has been heated to 60° to 80° C. and may contain sodium hydroxide solution, and the resulting suspension or solution is brought to ph 7–8. Thereafter the pH is buffered to 8–9 and oxidizing agent is added. After the cyanide ion donor compound has been added, the reaction with the cyanide ions to give diaminodinitrile takes place at from 60° to 95° C. The end of the reaction is readily detectable by thin layer chromatography. After excess cyanide has been destroyed, for example with hydrogen peroxide, the reaction mixture is filtered, and the residue is washed with water and dried. The reaction medium used according t the invention is a mixture of water and 1-methoxy-2-propanol, 2-methoxy-1-propanol, dimethylformamide, N-methylpyrrolidone, dimethyl sulfoxide, dimethylacetamide, dimethylpropionamide or dioxane or a mixture thereof. The organic liquid is preferably 1-methooxy-2-propanol, dimethylformamide, dimethylacetamide, N-methylpyrrolidone, dimethyl sulfoxide or dioxane. The ratio water:organic liquid is $\geq 3:1$, preferably from 10:1 to 4:1. Accordingly, the organic liquid is present in the reaction medium in an amount from about 7.5, preferably from 9, to 20% by weight, based on the medium. Higher concentrations of organic liquid are not diadvantageous, but do not produce any advantages either.

The amount of reaction medium ranges in general from 2.5 to 5 times weight of diaminoacid. The amount of sodium hydroxide solution is advantageously chosen to be such that the sulfonic acid is virtually neutralized and dissolves. Thereafter the solution is brought to a pH from 7 to 8 by addition of further sodium hydroxide solution or, alternatively, acid. The mixture is then buffered to the pH range from 8 to 9 required for the start of the reaction. A buffer substance of good utility is sodium hydrogencarbonate, which is added to the solution at pH 7-8 in an amount from 50 to 100% by weight, preferably from 60 to 80% by weight, based on the diaminoacid used. Instead of sodium bicarbonate it is also possible to use hydrogenphosphates or easily hydrolyzable esters such as ethylene glycol acetate as buffers. The reaction takes place within the pH range 8 to 11. At ph > 11 there is an increasing tendency for the cyano groups in the diaminodinitrile to become hydrolyzed, thereby reducing the yield. At the end of the reaction the pH is within the range from 9 to 10.

The oxidizing agent used is advantageously the sodium salt of m-nitrobenzenesulfonic acid. However, it is also possible to use air, which is passed through the reaction mixture during the reaction. Since, in the course of the air being passed through, hydrogen cyanide escapes with the air and this hydrogen cyanide needs to be destroyed, this version of the process is less advisable.

The cyanide ion donor compound used is preferably an alkali metal cyanide. Since the handling of solid cyanides in larger quantities is problematic, in general from 20 to 30% strength by weight aqueous solutions are used. The water introduced in this way into the reaction mixture must be taken into account in dimensioning the amount of organic liquid. The amount of cyanide donor compound ranges from 3 to 5 moles of sodium cyanide per mole of diaminoacid.

The reaction takes place at from 60° to 100° C., preferably at from 90° to 95° C. and under the stated conditions is in general complete within from 3 to 7 hours. At higher temperatures there is an increased tendency for the cyano groups in the diaminodinitrile to become hydrolyzed, thereby reducing the yield.

The working Examples with follow will additionally explain the invention. Parts and percentages are by weight.

EXAMPLE 1

To a hot mixture at 80° C. of 160 parts of water and 20 parts of 1-methoxy-2-propanol are added 65.4 parts of 1,4-diaminoanthraquinone-2-sulfonic acid (diaminoacid: purity: 91.7%). The suspension is brought to pH 7.5-8.0 with 16 parts of 50% strength sodium hydroxide solution, and the sulfonic acid dissolves completely. After addition of 15.6 parts of the sodium salt of m-nitrobenzenesulfonic acid, 48 parts of sodium hydrogencarbonate and 37.2 parts of sodium cyanide, the mixture is heated to 90° C. and is stirred at that temperature for 7 hours. Conversion of the starting sulfonic acid is then complete, judging by thin layer chromatography.

After cooling down to 60° C., excess sodium cyanide is destroyed by adding 35 parts of 30% strength hydrogen peroxide at a time. The hot suspension is filtered with suction, and the residue is washed with hot water and dried at 100° C.

Yield: 53.9 parts of diaminodinitrile having a purity of 81.5% and a mononitrile content of 2.4%. The yield corresponds to 80.8% of theory.

EXAMPLE 2

To a hot solution at 80° C. of 84 parts of water and 20 parts of 1-methoxy-2-propanol are added 65.4 parts of diaminoacid (purity: 91.7%), and the resulting mixture is brought to ph 7.5-8.0 with about 16 parts of 50% strength sodium hydroxide solution. Thereafter 15.6 parts of the sodium salt of m-nitrobenzenesulfonic acid, 48 parts of sodium hydrogencarbonates and 124 parts of a 30% strength aqueous sodium cyanide solution are added. After 5 hours + stirring at 90° C. the reaction has ended, and the batch is worked up as in Example 1.

Yield: 53.2 parts of diamonodintrile having a purity of 82.3%; the yield corresponds to 80.6% of theory, based on starting sulfonic acid. Mononitrile content: 2.8%.

EXAMPLE 3

To a hot mixture at 60° C. of 738 parts of 1-methoxy-2-propanol, 600 parts of 50% strength sodium hydroxide solution and 2,960 parts of water are added 2,616 parts of 1,4-diaminoanthraquinone-2-sulfonic acid (purity: 91.7%). The mixture is brought to pH 7.5-8.0 with 60 parts of 50% strength sodium hydroxide solution. Thereafter 650 parts of the sodium salt of m-nitrobenzenesulfonic acid, 1,520 parts of sodium hydrogencarbonate and finally 4,960 parts of a 30% strength aqueous cyanide solution are added, and the reaction mixture is heated to 90° C. After 5 hours + stirring at 90° C. conversion of the sulfonic acid is complete. The pH is 9.5. The reaction batch is worked up as in Example 1.

Yield: 2,180 parts of 1,4-diaminoanthraquinone-2,3-dicarbonitrile having a purity of 81.1%. The yield corresponds to 81.3% of theory, based on the pure sulfonic acid. The mononitrile content is 2.1%.

EXAMPLES 4 TO 8

Example 1 is repeated, except that the 20 parts of 1-methoxy-2-propanol are replaced in each case by 20 parts of the solvents indicated in column 2 of the Table.

This Table also shows the yield and purity of the diaminodinitrile obtained and the mononitrile content thereof.

|  | Solvent | Diaminodinitrile | | Mononitrile content % |
|---|---|---|---|---|
|  |  | Yield % of th. | Purity % |  |
| Example 4 | Dimethylacetamide | 80.4 | 83.1 | 3.2 |
| Example 5 | N—methylpyrrolidone | 81.8 | 84.0 | 2.2 |
| Example 6 | Dimethylformamide | 80.4 | 83.1 | 3.7 |
| Example 7 | Dioxane | 76.3 | 81.3 | 2.7 |
| Example 8 | Dimethyl sulfoxide | 79.4 | 80.0 | 3.2 |

COMPARATIVE EXAMPLE 1

A suspension of 65.4 parts of 1,4-diaminoanthraquinone-2-sulfonic acid (purity: 91.7%) in 180 parts of water is brought to ph 7.5-8.0 with 50% strength sodium hydroxide solution, which requires 16 parts thereof. 15.6 parts of the sodium salt of m-nitrobenzenesulfonic acid, 48 parts of sodium hydrogencarbonate, 0.4 part of ammonium vanadate and 37.2 parts of sodium cyanide are then added to the solution which is formed. After 20 hours' stirring at 90° C. the batch is worked up as in Example 1.

45.6 parts were isolated of diaminodinitrile having a purity of 78.7% and a mononitrile content of 9.9%, corresponding to a yield of 66% of theory.

COMPARATIVE EXAMPLE 2

To a mixture of 160 parts of water, 20 parts of ethylene glycol and 15 parts of 50% strength sodium hydroxide solution are added at 60° C. 65.4 parts of 1,4-diaminoanthraquinone-2-sulfonic acid (purity: 91.7%). The pH is adjusted to 7.5–8.0 with further sodium hydroxide solution. To the blue solution are added 15.6 parts of sodium m-nitrobenzenesulfonate, 38 parts of sodium bicarbonate and 37.2 parts of sodium cyanide, and the temperature is raised to 90° C. The reaction is still not complete after 24 hours, judging by thin layer chromatograpy.

Working up as in Example 1 isolates 45.6 parts of 1,4-diaminodinitrile having a purity of only 69%.

COMPARATIVE EXAMPLE 3

Comparative Example 2 is repeated, except that the ethylene glycol is replaced by 20 parts of triethylene glycol monobutyl ether. The reaction is complete after 8 hours stirring at 90° C.

The reaction mixture is worked up as in Example 1. Yield: 45.3 parts of diaminodinitrile having a purity of 72.8%; this corresponds to a yield of 60% of theory.

COMPARATIVE EXAMPLES 3 TO 14

Comparative Example 2 is repeated, except that the ethylene glycol is replaced by 20 parts of the solvents indicated in column 2 of the Table below. The Table also lists the yield and purity of the resulting dinitrile and the mononitrile content thereof.

| Comparative Example | Solvent | Diaminodinitrile Yield % of th. | Purity % | Mononitrile content % |
|---|---|---|---|---|
| 4 | Ethylene glycol monomethyl ether | 68.2 | 69 | 4.5 |
| 5 | Diethylene glycol monomethyl ether | 67.8 | 70.4 | 3.5 |
| 6 | Ethylene glycol monobutyl ether | 68.0 | 71.6 | 4.2 |
| 7 | Diethylene glycol monobutyl ether | 65.2 | 75.4 | 3.6 |
| 8 | Ethylene glycol monophenyl ether | 67.9 | 74.4 | 3.7 |
| 9 | n-Propanol | 67.6 | 73.2 | 1.7 |
| 10 | i-Butanol | 53.6 | 58.7 | 3.8 |
| 11 | n-Butanol | 52.8 | 69.0 | 4.2 |
| 12 | n-Pentanol | 46.8 | 72.7 | 5.2 |
| 13 | Dipropylene glycol monomethyl ether | 69.9 | 75.4 | 0.6 |
| 14 | Dipropylene glycol monoisopropyl ether | 57.9 | 75.5 | 4.0 |

We claim:

1. A process for preparing 1,4-diamino-2,3-dicyanoanthraquinone by reacting 1,4-diaminoanthraquinone-2-sulfonic acid or a salt thereof with cyanide ions in water within the pH range of from 8 to 9 in the presence of an oxidizing agent at elevated temperatures, which comprises carrying out the reaction in a mixture of water and one organic liquid selected from the group consisting of 1-methoxy-2-propanol, 2-methoxy-1-propanol and a mixture thereof, the ratio water:organic liquid being $\geq 3:1$ parts by weight.

2. A process as claimed in claim 1, wherein the organic liquid used is 1-methoxy-2-propanol.

3. A process as claimed in claim 1, wherein the ratio water:organic liquid ranges from 4:1 to 10:1 parts by weight.

4. A process as claimed in claim 2, wherein the ratio water:organic liquid ranges from 4:1 to 10:1 parts by weight.

5. A process as claimed in claim 1, wherein, based on 1,4-diaminoanthraquinone-2-sulfonic acid, from 2.5 to 5 times the weight of a mixture of water and organic liquid is used.

6. A process as claimed in claim 2, wherein, based on 1,4-diaminoanthraquinone-2-sulfonic acid, from 2.5 to 5 times the weight of a mixture of water and organic liquid is used.

7. A process as claimed in claim 3, wherein, based on 1,4-diaminoanthraquinone-2-sulfonic acid, from 2.5 to 5 times the weight of a mixture of water and organic liquid is used.

8. A process as claimed in claim 4, wherein, based on 1,4-diaminoanthraquinone-2-sulfonic acid, from 2.5 to 5 times the weight of a mixture of water and organic liquid is used.

9. A process as claimed in 2, wherein the reaction is carried out in the presence of sodium hydrogencarbonate as buffer.

10. A process as claimed in claim 4, wherein the reaction is carried out in the presence of sodium hydrogencarbonate as buffer.

11. A process as claimed in claim 8, wherein the reaction is carried out in the presence of sodium hydrogencarbonate as buffer.

12. A process as claimed in claim 7, wherein the ratio cyanide donor substance:1,4-diaminoanthraquinone-2-sulfonic acid ranges from 3:1 to 5:1 moles.

13. A process as claimed in claim 8, wherein the ratio cyanide donor substance:1,4-diaminoanthraquinone-2-sulfonic acid ranges from 3:1 to 5:1 moles.

14. A process as claimed in claim 11, wherein the ratio cyanide donor substance:1,4-diaminoanthraquinone-2-sulfonic acid ranges from 3:1 to 5:1 moles.

15. A process as claimed in claim 10, wherein the ratio cyanide donor substance:1,4-diaminoanthraquinone-2-sulfonic acid ranges from 3:1 to 5:1 moles.

16. A process as claimed in claim 7, wherein the reaction is carried out in the presence of m-nitrobenzenesulfonic acid as oxidizing agent.

17. A process for preparing 1,4-diamino-2,3-dicyanoanthraquinone by reacting 1,4-diaminoanthraquinone-2-sulfonic acid or a salt thereof with cyanide ions in water within the pH range of from 8 to 9 in the presence of an oxidizing agent at elevated temperature, which comprises carrying out the reaction in a mixture of water and 1-methoxy-2-propanol, the ratio water:organic liquid ranging from 4:1 to 10:1 parts by weight and the reaction being carried out in the presence of sodium hydrogencarbonate as a buffer and with a ratio cyanide donor substance:1,4-diaminoanthraquinone-2-sulfonic acid ranging from 3:1 to 5:1 moles.

18. A process as claimed in claim 17, wherein the reaction is carried out in the presence of m-nitrobenzenesulfonic acid (sodium salt).

* * * * *